United States Patent [19]

Hasegawa et al.

[11] Patent Number: 5,458,681
[45] Date of Patent: Oct. 17, 1995

[54] ORGANOSILICON-TREATED PIGMENT, PROCESS FOR PRODUCTION THEREOF, AND COSMETIC MADE THEREWITH

[75] Inventors: Yukio Hasegawa, Kasukabe; Ryota Miyoshi, Yono; Isao Imai, Kuki, all of Japan

[73] Assignee: Miyoshi Kasei Co., Ltd., Urawa, Japan

[21] Appl. No.: 181,114

[22] Filed: Jan. 13, 1994

Related U.S. Application Data

[63] Continuation-in-part of Ser. No. 903,225, Jun. 25, 1992, Pat. No. 5,368,639.

[30] Foreign Application Priority Data

Jun. 26, 1991 [JP] Japan ..................... 3-250164
Jun. 8, 1992 [JP] Japan ..................... 4-173861

[51] Int. Cl.$^6$ ............................ C04B 14/04; A61K 7/00
[52] U.S. Cl. ............... 106/490; 106/287.11; 106/287.12; 106/287.13; 106/465; 106/493; 424/69; 424/78.03; 428/405; 428/447
[58] Field of Search ............... 106/490, 287.11, 106/287.12, 287.13, 465, 493; 424/69, 78.03; 428/405, 447

[56] References Cited

U.S. PATENT DOCUMENTS

| | | | |
|---|---|---|---|
| 3,377,311 | 4/1968 | Roch | 523/213 |
| 4,891,392 | 1/1990 | Abe et al. | 523/200 |
| 5,001,183 | 3/1991 | Sands et al. | 524/493 |
| 5,013,585 | 5/1991 | Shimizu et al. | 427/220 |
| 5,118,496 | 6/1992 | Herstein | 424/63 |

FOREIGN PATENT DOCUMENTS 61-283637-A  12/1986  Japan ..................... 106/490

OTHER PUBLICATIONS

Derwent abstract 87-26316/04 of JP 61-283637 to Hikawa, Dec. 1986.
JAPIO abstract 86-283637 of JP 61-283637 (Hikawa), Dec. 1986.

*Primary Examiner*—Mark L. Bell
*Assistant Examiner*—Scott L. Hertzog
*Attorney, Agent, or Firm*—Armstrong, Westerman, Hattori, McLeland & Naughton

[57] ABSTRACT

A pigment or extender pigment treated with a linear reactive alkylpolysiloxane having in the molecule amino groups, imino groups, halogen atoms, hydroxyl groups, or alkoxyl groups, which is oriented and adsorbed to the surface of the pigment or extender pigment by heat treatment; a process for producing the treated pigment; and a cosmetic made with the treated pigment. The alkylpolysiloxane has a degree of polymerization from 25 to 100 and a Mw/Mn ratio from 1.0 to 1.3. The organosilicon-treated pigment, characterized by silicone firmly adsorbed to its surface, freedom from residual hydrogen, very smooth feel, good adhesion to the skin, and ability to permit color pigment of fine particle size to spread well, is particularly suitable for use in cosmetics such as powder foundation, liquid foundation, rouge, and eye shadow.

5 Claims, 1 Drawing Sheet

ORGANOSILICON-TREATED PIGMENT, PROCESS FOR PRODUCTION THEREOF, AND COSMETIC MADE THEREWITH

This application is a continuation-in-part of application Ser. No. 07/903,225, filed Jun. 25, 1992, which issued as U.S. Pat. No. 5,368,639.

BACKGROUND OF THE INVENTION

1. Field of the Invention

The present invention relates to an organosilicon-treated pigment, a process for production thereof, and a cosmetic made therewith, and more particularly, to a new pigment and new extender pigment which are smooth, superior in adhesion and spreadability, and completely free of residual hydrogen, a process for production of said pigment, and a cosmetic made with said pigment.

2. Description of the Prior Art

Organosilicon compounds, especially methylhydrogenpolysiloxane, have been used as surface treatment agents for pigments and extender pigments. The surface-treated pigments are now generally used for long-lasting makeup and two-way type cosmetics because of their high water repellency.

The ordinary method for surface treatment does not permit the reactive Si—H groups of the silicone molecule to undergo complete reaction. The percent conversion is such that 30–60% of hydrogen remains unreacted. This holds true of methylhydrogenpolysiloxane. Its crosslinking reaction does not proceed completely on account of steric hindrance, with hydrogen remaining unreacted. Pigments or extender pigments with such residual hydrogen give off gaseous hydrogen (which presents a danger of explosion) upon processing into cosmetics under alkaline or acidic conditions. Moreover, the resulting cosmetics cause expansion of their containers or cloud the compact glass as time goes by.

Those pigments vulnerable to heat, such as yellow oxide, Prussian blue, and Red 202 (Lithol Rubine BCA), may be treated at a low temperature with the aid of a catalyst. A disadvantage of this method is that the catalyst remains unreacted.

There has been proposed a process for treatment with methylhydrogenpolysiloxane to improve the percent conversion by addition of an acid substance or an alkali metal hydroxide. A disadvantage of this process is that methylhydrogenpolysiloxane undergoes crosslinking polymerization which gives rise to silicone resin of reticulate three-dimensional structure. This silicone resin forms particles, which in turn brings about the strong coagulation of pigment particles. Therefore, the resulting treated pigment feels rough and is very poor in spreadability and adhesion to the skin.

Another improvement is by mechanochemical treatment that employs a jet atomizer. The percent conversion of methylhydrogenpolysiloxane by this method is still as low as 20–70%, depending on the kind of pigment used for treatment. Hence, the above-mentioned problem associated with residual hydrogen remains unsolved. Moreover, the mechanochemical treatment resorting to crushing deforms the particles of pigment or extender pigment. This is disadvantageous to a pigment or extender pigment composed of flaky or needlelike particles. In addition, the mechanochemical treatment requires special facilities which are not suitable for production of a variety of products in small quantities.

SUMMARY OF THE INVENTION

The present invention was completed to solve the above-mentioned problem. It is an object of the present invention to provide an organosilicon-treated pigment which is characterized by smooth feel, good adhesion to the skin, no coagulation and no residual hydrogen, and ability to provide a very high saturation and tone when mixed with color pigment. It is another object of the present invention to provide an organosilicon-treated pigment which can be produced in a simple manner from any heat-vulnerable pigment at a low temperature without the aid of catalyst and using existing equipment unmodified. It is further another object of the present invention to provide a process for the production of said treated pigment and a cosmetic which contains said treated pigment.

The gist of the present invention resides in an organosilicon-treated pigment which comprises a pigment or extender pigment and a linear reactive alkylpolysiloxane having in the molecule amino groups, imino groups, halogen atoms, hydroxyl groups, or alkoxyl groups, which is oriented and adsorbed to the surface of the pigment or extender pigment by heat treatment.

DETAILED DESCRIPTION OF THE INVENTION

According to the present invention, the organosilicon-treated pigment is made with a linear reactive alkylpolysiloxane which has at the terminal of the molecular chain such reactive groups as amino group (—$NH_2$), imino group (=NH), halogen atom (e.g., Cl, Br, and I), hydroxyl group (—OH), and alkoxyl group (—OR, where R denotes an alkyl group). It should have a degree of polymerization (n) of 7–1000, preferably 25–100, and more preferably 30–50. If the degree of polymerization is below 25, the alkylpolysiloxane often does not exhibit the characteristics of a silicone, such as water repellency, smoothness and like, and if the degree of polymerization is over 100, the alkylpolysiloxane tends to have poor reactivity with the surface of the pigment or extender pigment.

The ratio of weight-average molecular weight (Mw) to number-average molecular weight (Mn), (Mw/Mn), is generally called the degree of dispersion of molecular weight. According to the present invention, the degree of dispersion of molecular weight of the alkylpolysiloxane must be from 1.0 to 1.3, preferably from 1.15 to 1.21). This is because a degree of dispersion of molecular weight of less than 1.0 cannot exist theoretically. On the other hand, when the degree of dispersion is over 1.3, the range of molecular weight becomes too wide. In such case, where the reactive alkylpolysiloxane is oriented and adsorbed to the surface of the pigment, the characteristics of the present invention, especially, the smooth feel and good adhesion sought in the present invention, cannot be obtained.

Figure 1A:
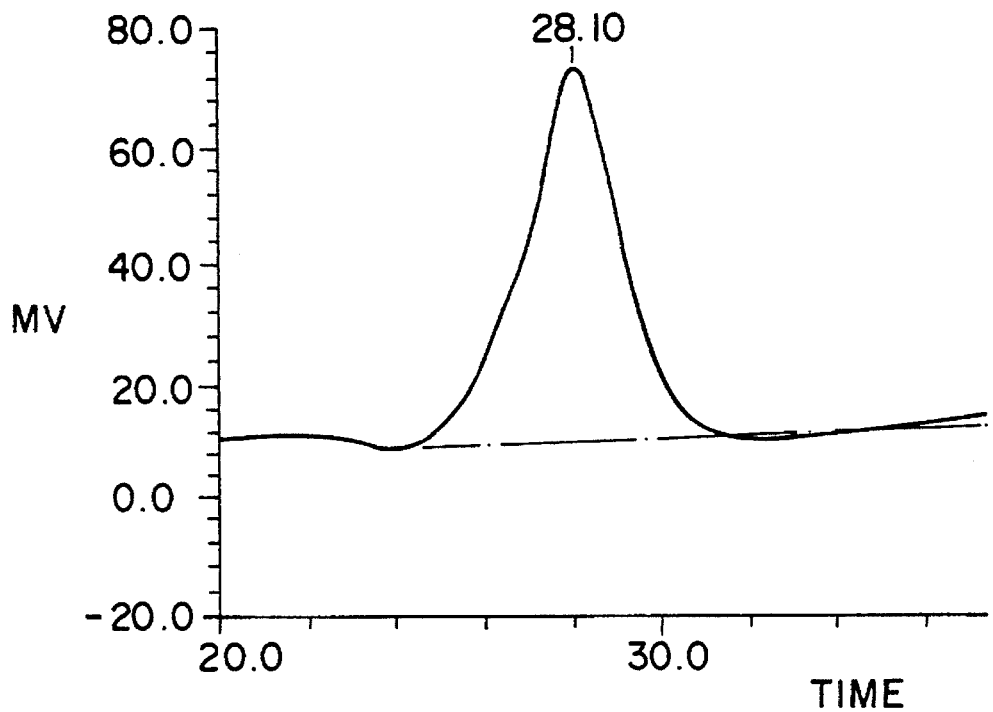
FIG. 1(a) is a chromatogram of a silicone suitable for use in the present invention.
Figure 1B:
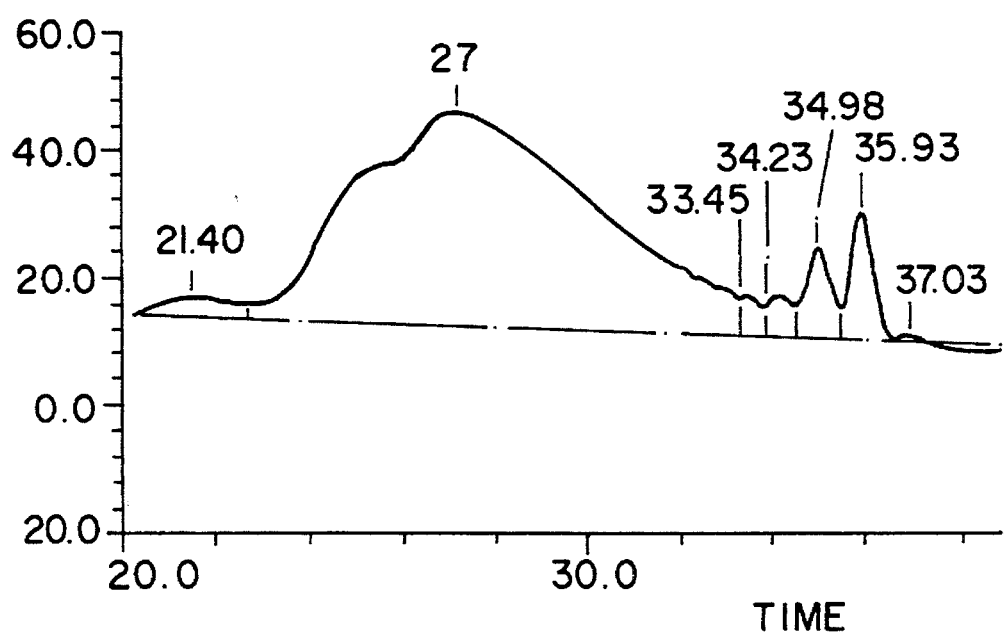
FIG. 1(b) is a chromatogram of a silicone unsuitable for use in the present invention.

The degree of dispersion of molecular weight may be determined by a conventional method with the aid of gel permeation chromatography (GPC). The degree of dispersion of molecular weight of many silicones which are commercially available is generally between the range of 1.4 to 2.0. According to the present invention, the degree of dispersion of molecular weight of silicone should be 1.0 to 1.3, a silicone having such a degree of dispersion being called a monodisperse silicone. A chromatogram (GPC chart) of a monodisperse silicone used in the present invention and that of a conventional silicone oil are shown in FIGS. 1(a) and 1(b). FIG. 1(a) is a chart for a monodisperse silicone according to the present invention, which has a degree of dispersion of molecular weight of 1.17. FIG. 1(b) is a chart for a conventional silicone having a degree of dispersion of molecular weight of 1.9. In the GPC charts shown in FIGS. 1(a) and 1(b), the abscissa axis represents the amounts of eluate and the ordinate axis represents the concentration of the dissolved substance. As shown in FIG. 1(a), the silicone of the present invention shows a sharp peak in the GPC chart.

Examples of suitable alkylpolysiloxanes include dimethylpolysiloxysilazane, α-monohydroxysiloxane, αω-dihydroxypolydimethylsiloxane, α-monoalkoxypolydimethylsiloxane, α, ω-dihdroxypolydimethylsiloxane, α-dialkoxypolydimethylsiloxane, α-trialkoxypolydimethylsiloxane, α, ω-hexa-alkoxypolydimethylsiloxane, dimethylpolysiloxy chloride, dimethylpolysiloxy bromide, and dimethylpolysiloxy iodide. Preferred among those examples are α-monoalkoxypolydimethylsiloxane, α-dialkoxypolydimethylsiloxane, and α-trialkoxypolydimethylsiloxane. They are adsorbed to the pigment very easily, and upon adsorption they impart a smooth feel to the treated pigment. The reactive group in the alkylpolysiloxane may be joined to the silicon atom directly or indirectly thorough a substituent group.

The pigment or extender pigment in the present invention embraces inorganic pigments (such as titanium oxide, zinc oxide, zirconium oxide, yellow iron oxide, black iron oxide, red iron oxide, ultramarine, Prussian blue, chromium oxide, and chromium hydroxide), iridescent pigments (such as titanium mica and bismuth oxychloride), organic dyestuffs (such as tar dyestuffs and natural dyestuffs), and powder (such as silica beads, plastic (nylon or polyacryl) beads, talc, kaolin, white mica, sericite, other micas, magnesium carbonate, calcium carbonate, aluminum silicate, magnesium silicate, calcium silicate, clay and the like). Preferred among those examples are fine particles or superfine particles (smaller than 1 μm in diameter) of titanium oxide and color pigments (such as yellow iron oxide, black iron oxide, red iron oxide, ultramarine, Prussian blue, chromium oxide, chromium hydroxide, tar dyestuffs and the like). They are superior in adhesion and spreadability.

According to the present invention, the organosilicon compound (or the linear reactive alkylpolysiloxane) should be used in an amount of 0.1–30 wt %, preferably 2–5 wt %, of the pigment or extender pigment to be treated, depending on its particle diameter and specific surface area.

According to the present invention, the organosilicon-treated pigment is produced by mixing a linear reactive alkylpolysiloxane as specified above, an organic solvent which dissolves said polysiloxane, and a pigment or extender pigment, and drying the mixture by heating.

A proper organic solvent should be selected in consideration of its flash point and ignition point, and the surface activity and heat stability of the pigment or extender pigment for surface treatment. Preferred examples of the organic solvent include ethers, ketones, halogenated hydrocarbons, aliphatic hydrocarbons, and alcohols and mixture thereof with other solvents such as water. The organic solvent should be used in an amount of 1–50 wt % to the pigment or extender pigment.

The mixing of the reactive alkylpolysiloxane, organic solvent, and pigment or extender pigment may be accomplished by putting them together into an ordinary mixer, or by spraying the reactive alkylpolysiloxane onto a mixture of the organic solvent and pigment or extender pigment. The heating of the mixture should be carried out in an adequate manner in consideration of the heat resistance of the pigment or extender pigment and the kind of organic solvent used.

The present invention also provides a cosmetic which contains the organosilicon-treated pigment mentioned above. The term "cosmetic" encompasses make-up such as powder foundation, liquid foundation, rouge, eye shadow, and the like, as well as basic cosmetics, hair preparations and nail enamels.

As mentioned above, the organosilicon-treated pigment of the present invention is one which comprises a pigment or extender pigment and a linear reactive alkylpolysiloxane which is oriented and adsorbed to the surface of the pigment or extender pigment by heat treatment. The linear reactive alkylpolysiloxane readily adheres to and reacts with a variety of powder as the pigment, whereas it does not undergo crosslinking polymerization leading to a three-dimensional structure. Therefore, it permits the surface treatment of heat-vulnerable pigments under mild conditions without the aid of catalyst. The resulting treated pigment has a smooth feel and is superior in adhesion to the skin and is free from coagulation. Although the surface treatment is accompanied by ammonia and hydrogen chloride, they are released upon heating, leaving no residue. The treated pigment with outstanding properties as mentioned above is used to make a cosmetic having good adhesion. Particularly, it imparts a highly saturated tone to a cosmetic containing the treated pigment.

EXAMPLES

The invention will be described in more detail with reference to the following examples, in which "parts" means "parts by weight".

Organosilicon-Treated Pigment

Example 1

100 g of talc (JA-46R made by Asada Seifun Co., Ltd.) and 8 g of benzene were mixed with each other for 5 minutes using a home mixer. The mixture was further mixed with 2 g of dimethylpolysiloxysilazane (n=30; Mw/Mn=1.15) by spraying for 5 minutes. The mixture was dried at 80° C. to remove benzene completely and then heated at 115° C. for 3 hours. Thus there was obtained a treated pigment having a smooth feel and good adhesion.

Comparative Example 1

The same procedure as in Example 1 was repeated except that the dimethylpolysiloxysilazane was replaced by methylhydrogenpolysiloxane. The resulting treated pigment was poor in adhesion notwithstanding its smooth feel.

Example 2

100 of calcined mica (having an average particle size of 5 μm), 25 g of a 2:1 mixture of water and isopropyl alcohol, and 3 g of α-triethoxypolydimethylsiloxane (n=30; Mw/Mn=1.19) were mixed with one another for 5 minutes using a home mixer. The mixture was heated at 115° C. for 6 hours. Thus there was obtained a mica powder having polydimethylsiloxane oriented and adsorbed to the surface thereof. This powder has a much smoother feel than the calcined mica (having an average particle size of 5 μm) surface-treated with methylhydrogenpolysiloxane. In addition, it has a moist feel and yet exhibits strong water repellency.

Cosmetics

Example 3

A powder foundation of the following formulation was prepared.

| Component I | |
|---|---|
| Talc | 35.0 parts |
| Scricite | 20.0 parts |
| Mica powder | 15.0 parts |
| Titanium oxide | 7.0 parts |
| Titanium oxide (fine particle) | 5.0 parts |
| Yellow iron oxide | 3.5 parts |
| Black iron oxide | 0.5 parts |
| Red iron oxide | 2.0 parts |
| Component 2 | |
| Liquid paraffin | 5.0 parts |
| Stearyl alcohol | 3.0 parts |
| Beeswax | 3.0 parts |
| Squalene | 1.0 part |

Component 1, which is a mixture of pigments and extender pigments, was surface-treated with dimethylpolysiloxysilazane by the method of Example 1. The treated pigments were mixed with one another using a Henschel mixer and then ground using an atomizer. The ground product was mixed with Component 2 (which had been heated) using a Henschel mixer and then ground again using an atomizer. The ground product was filled into a cosmetic container to form a desired product (powder foundation). This powder foundation exhibited very good spreadability, adhesion, color saturation and water repellency.

Comparative Example 2

The same procedure as in Example 3 was repeated except that the dimethylpolysiloxysilazane for surface treatment was replaced by methylhydrogenpolysiloxane. The obtained powder foundation exhibited mediocre spreadability and adhesion, and less color saturation than the powder foundation of Example 3.

Comparative Example 3

The same procedure as in Example 3 was repeated except that 100 g of Component 1 (which is a mixture of pigments and extender pigments) underwent grinding in a ball mill for 5 hours, and further underwent grinding together with 5 g of methylhydrogenpolysiloxane for 5 hours. The obtained powder foundation exhibited poor spreadability and adhesion, and mediocre color saturation.

Each of the treated pigments prepared in Example 3 and Comparative Examples 2 and 3 was ground twice using an atomizer, and the ground product was made into a sample of powder foundation. It was tested for spreadability, adhesion, color saturation, and water repellency in the same manner as mentioned above. Similar tests were conducted with each pigment ground three times.

The results show that, in the case of conventional silicone treatment, the powder foundation improves in color saturation but becomes poor in spreadability, adhesion, and water repellency in proportion to the number of repetitions of crushing by an atomizer. In contrast, in the case of the silicone treatment according to the present invention, the powder foundation remains unaffected by the repeated crushing by an atomizer.

Example 4

A liquid foundation of the following formulation was prepared.

| Component A | |
|---|---|
| Cyclomethycon | 12.0 parts |
| Emulsified volatile oil | 2.0 parts |
| Titanium oxide | 9.0 parts |
| Red iron oxide | 0.7 parts |
| Yellow iron oxide | 0.2 parts |
| Black iron oxide | 3.0 parts |
| Talc | 2.0 parts |
| Component B | |
| Propylparaben | 0.2 parts |
| Polyoxyethylene lauryl ether | 0.5 parts |
| Component C | |
| Emulsified volatile oil | 18.0 parts |
| Dimethylsilicone (50 cs.) | 3.0 parts |
| Tocopherol acetate | 0.1 part |
| Corn oil | 0.05 part |
| Component D | |
| Methylparaben | 0.2 part |
| Propylene glycol | 8.0 parts |
| Component E | |
| Sodium dehydroacetate | 0.3 part |
| Pantothenyl alcohol | 0.2 part |
| Sodium chloride | 2.0 parts |
| Purified water (to make 100 parts) | Balance |

First, Component A, which is a mixture of pigments and extender pigments, was surface-treated with dimethylpolysiloxysilazane (2%) in the same manner as in Example 1. Component A was mixed with Components B and C, which had been melted by heating at 60° C. Components D and E were mixed with each other after melting by heating at 60° C. To the first mixture was slowly added the second one with stirring to effect emulsification. Upon cooling, there was obtained a sample of liquid foundation.

Comparative Example 4

The same procedure as in Example 4 was repeated to prepare a sample of liquid foundation except that the dimethylpolysiloxysilazane for surface treatment was replaced by methylhydrogenpolysiloxane.

The sample of liquid foundation obtained in Example 4 and Comparative Example 4 were stored in polyethylene bottles for 1 mont to see if they change in the time and liberate hydrogen. The liberated hydrogen was detected by means of a hydrogen detector tube.

No hydrogen was liberated by the sample according to the present invention, whereas the comparative sample treated with a conventional silicone was found to liberate hydrogen. This result suggests that the cosmetic of the present invention is superior in stability and feel to the conventional one.

Each of the treated pigments prepared in Example 3 and Comparative Examples 2 and 3 was tested for the dissolution of silicone in chloroform.

Test method:

To 20 g of sample (treated pigment) was added 100 ml of chloroform. After stirring for 30 minutes, the dispersion was filtered through a glass filter. The solid was washed twice with 20 ml of chloroform. The filtrate was dried at 100° C. for 10 hours and then at 120° C. for 1 hour, and the amount of the extracted silicone was accurately measured. It was found that the amount of silicone extracted from the pigment according to the present invention is much less than that extracted from the comparative pigments prepared by conventional methods. This result suggests that silicone is firmly adsorbed to pigment in the case of surface treatment according to the present invention.

The organosilicon compound used in the present invention, which covers the pigment, has a reactive group at one end which causes it to be oriented and adsorbed to the pigment firmly in a specific direction. In addition, due to its specific polymerization degree and extremely narrow range of molecular weight distribution, the organosilicone compound has a uniform molecular chain length. Therefore, the pigment treated according to the present invention with the organosilicon compound has an extremely smooth feel.

Thus, the present invention provides an organosilicon-treated pigment which is characterized by silicone firmly adsorbed to the surface of a pigment or extender pigment, freedom from residual hydrogen, very smooth feel, good adhesion to the skin, and superior ability to permit color pigment of fine particle size to spread well. The treated pigment having such outstanding properties finds use as a component of high-quality cosmetics including basic cosmetics, makeup cosmetics (such as powder foundation, liquid foundation, rouge, eye shadow), hair cosmetics and nail enamels.

We claim:

1. An organosilicon-treated pigment or extender pigment comprising a pigment or extender pigment treated with a linear reactive alkylpolysiloxane having a degree of polymerization from 25 to 100, and a ratio (Mw/Mn) of weight-average molecular weight (Mw) to number-average molecular weight (Mn) from 1.0 to 1.3, and having at one end of its molecular chain a group selected from the group consisting of amino, imino, halogen, hydroxyl, and alkoxyl, wherein said alkylpolysiloxane is oriented and adsorbed to the surface of the pigment or extender pigment.

2. An organosilicon-treated pigment or extender pigment as in claim 1, wherein the alkylpolysiloxane has a degree of polymerization from 30 to 50.

3. An organosilicon-treated pigment or extender pigment as in claim 1, wherein the alkylpolysiloxane has a Mw/Mn ratio from 1.15 to 1.21.

4. A process for producing an organosilicon-treated pigment or pigment extender, comprising mixing a linear reactive alkylpolysiloxane with an organic solvent capable of dissolving the alkylpolysiloxane and with a pigment or extender pigment, and drying the resulting mixture by heating, wherein the alkylpolysiloxane has at one end of its molecular chain a group selected from the group consisting of amino, imino, halogen, hydroxyl and alkoxyl, and the alkylpolysiloxane has a degree of polymerization from 25 to 100, and a ratio (Mw/Mn) of weight-average molecular weight (Mw) to number-average molecular weight (Mn) from 1.0 to 1.3.

5. A cosmetic comprising the organosilicon-treated pigment or extender pigment of claim 1.

* * * * *